United States Patent [19]

Hon et al.

[11] Patent Number: 4,920,966

[45] Date of Patent: May 1, 1990

[54] ULTRASOUND TRANSDUCER HOLDER

[76] Inventors: Edward H. Hon, 11 Bradbury Hills Rd., Bradbury, Calif. 91010; Edward D. Hon, 1325 6th Ave., San Francisco, Calif. 94122; Robert W. Hon, 483 Panchita Way, Los Altos, Calif. 94022

[21] Appl. No.: 162,033

[22] Filed: Feb. 29, 1988

Related U.S. Application Data

[63] Continuation-in-part of Ser. No. 915,130, Oct. 2, 1986.

[51] Int. Cl.[5] ............................................. A61B 8/00
[52] U.S. Cl. ............................... 128/662.03; 128/775
[58] Field of Search ............................ 128/660–663, 128/639–641, 643–644, 744–775, 778, 780, 782, 798, 802–803, 672, 691, 661.07–661.10, 662.01, 662.03–662.04

[56] References Cited

U.S. PATENT DOCUMENTS

| | | | |
|---|---|---|---|
| 3,420,223 | 1/1969 | Day et al. | 128/639 |
| 3,545,432 | 12/1970 | Berman | 128/640 |
| 3,859,984 | 1/1975 | Langley | 128/661 |
| 4,209,020 | 6/1980 | Nielsen | 128/641 X |
| 4,332,257 | 6/1982 | Ayer | 128/641 X |
| 4,355,643 | 10/1982 | Laughlin et al. | 128/663 |
| 4,503,861 | 3/1985 | Entrekin | 128/661 |
| 4,538,617 | 9/1985 | Jensen | 128/640 X |
| 4,556,066 | 12/1985 | Semrow | 128/661 X |
| 4,657,022 | 4/1987 | Holscher | 128/640 X |

FOREIGN PATENT DOCUMENTS 0919658  4/1982  U.S.S.R. ............................. 128/643

OTHER PUBLICATIONS

Published Article entitled, "Diagnosis and Treatment of Fetal Disorders", pp. 185–203, By Edward Hon (1968). Corrometrics Medical Systems, Inc.; Fetal Monitor Manual P/N 1121 AB, 9/84, pp. 19–24.

Primary Examiner—Angela D. Sykes
Attorney, Agent, or Firm—Lewis Anten

[57] ABSTRACT

A device for attaching an ultrasonic transducer to the body of a patient, particularly to obtain the fetal heart rate in a pregnant patient, that does not require the use of belts, is disclosed. The device is adhesively attached to the patient and permits the ultrasound transducer to be held in a desired orientation.

28 Claims, 2 Drawing Sheets

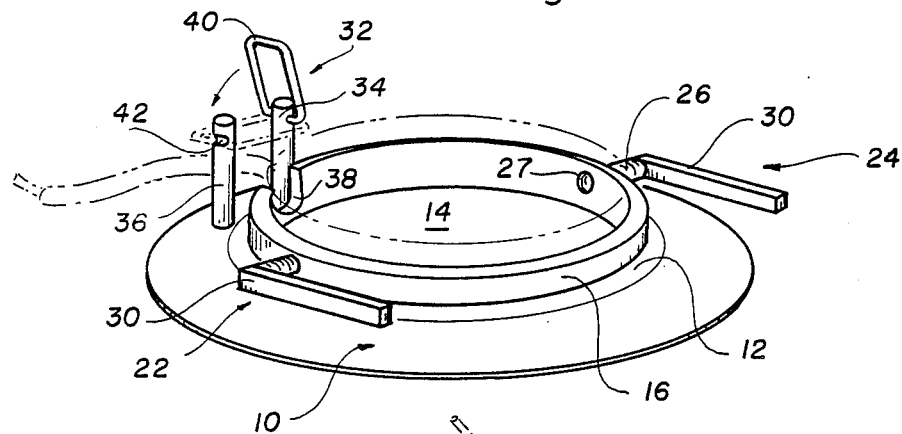
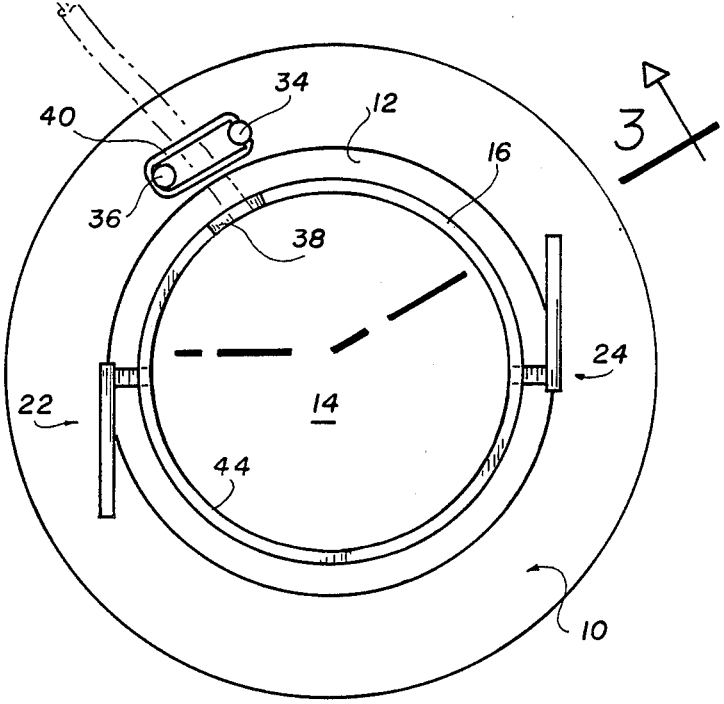
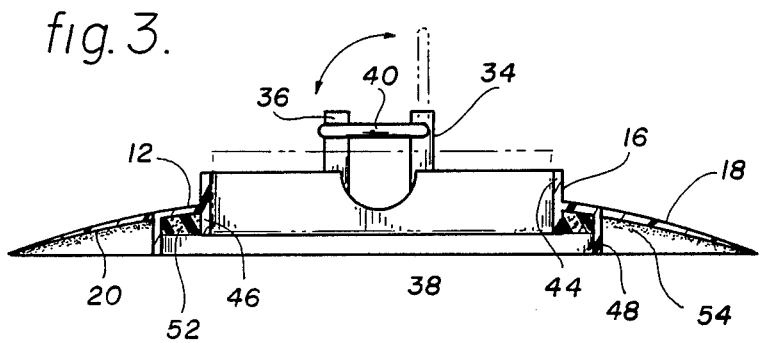

ULTRASOUND TRANSDUCER HOLDER

BACKGROUND

There are a number of medical tests that require the monitoring of a patient, and in particular the monitoring of a mother and the fetus during pregnancy, with an ultrasound transducer, e.g. obtaining the fetal heartbeat, as well as a number of other conditions that cannot be observed directly.

In use, a coupling gel is applied to the transducer face and the transducer is then moved over the area of the patient where the best data is obtained. The data is typically observed on a monitor, and/or is stored on hard storage media.

If data is to be obtained over a long period of time, some means of holding the ultrasound transducer in place is required. The present means of maintaining the ultrasound transducer on the patient is by using an encircling abdominal belt, as is commonly used for holding a tocodynamometer in place during the measurement of contractions.

Such belts when used with the ultrasound transducer are difficult to keep in place. The ultrasound transducer must be held in a desired position once the belt has been tightened and locked. Since the surface of the maternal abdomen is not uniform or flat, it is sometimes difficult to fix the orientation of the ultrasound transducer at the optimum angle to obtain the fetal heartbeat. Because the tension of the belt system holds the transducer face essentially parallel to the maternal abdomen wall, it is sometimes difficult to obtain the required data, and it becomes necessary to change this parallel orientation by angulating the transducer face. In the absence of a mechanical method to do this clinically, this is frequently done by inserting small pieces of material, such as wadded paper to achieve this end. Further, the abdomen of the pregnant woman does not maintain a constant shape during the testing period. The movement of the fetus, as well as contractions, cause the shape of the abdomen to change. This alters the pressure on the belt, causing it to slip and change position, thereby also causing the ultrasound transducer to change its position. The required data is thus frequently lost or its reliability is compromised. The instability of the procedure demands constant checking by the nursing and medical staff to make sure that the ultrasound transducer has not moved significantly.

In addition, with the belt system, it is not possible to have the patient move much during the time that data is being recorded, otherwise the position and/or orientation of the ultrasound transducer will be changed and the data compromised, or lost entirely. Even turning over in bed can cause total loss of data. However, during some tests, it is important to have the patient not only move, but also exercise while recording fetal heart rate data. Heretofore, there has been no apparatus that would permit the patient to exercise and still obtain good quality fetal heart rate recordings.

SUMMARY OF THE INVENTION

The present ultrasound transducer holder consists of a disc of relatively flexible material having a central ultrasound transducer support member made of a relatively rigid material having a central opening conforming to the periphery of the ultrasound transducer. An adhesive layer is applied to the lower surface of the disc, the adhesive being sufficiently strong to maintain the disc in place on the patient. A channel on the lower surface has an absorbent material, such as a sponge, which surrounds the central opening to prevent any gel or fluids from coming into contact with the adhesive and to assist in stabilizing the device.

The relatively rigid support member has means to grasp the ultrasound transducer and hold it in place. An additional grasping member is employed to grasp the external cable of the ultrasound transducer as well.

OBJECTS OF THE INVENTION

It is an object of the present invention to provide a means for applying an ultrasound transducer to a patient which does not require use of a belt.

It is another object of the present invention to provide a means for attaching an ultrasound transducer to a patient that is more reliable than existing devices.

It is yet another object of the present invention to provide a means for attaching an ultrasound transducer to a patient that will permit data to be obtained while the patient is moving.

It is still another object of the present invention to provide a means for attaching an ultrasound transducer to a patient that will permit the position of the ultrasound transducer to be maintained easily and reliably in a fixed position.

It is yet another object of the present invention to provide a means for attaching an ultrasound transducer to a patient that is simple to apply and use.

Further objects of the present invention will be evident from a reading of the following specification and the accompanying drawings.

BRIEF DESCRIPTION OF THE DRAWINGS

FIG. 1 is a top perspective view of the support of the present invention.

FIG. 2 is a top plan view of the support.

FIG. 3 is a side sectional view of the support taken along lines 3—3 of FIG. 2.

DETAILED DESCRIPTION OF THE INVENTION

Figure 4:
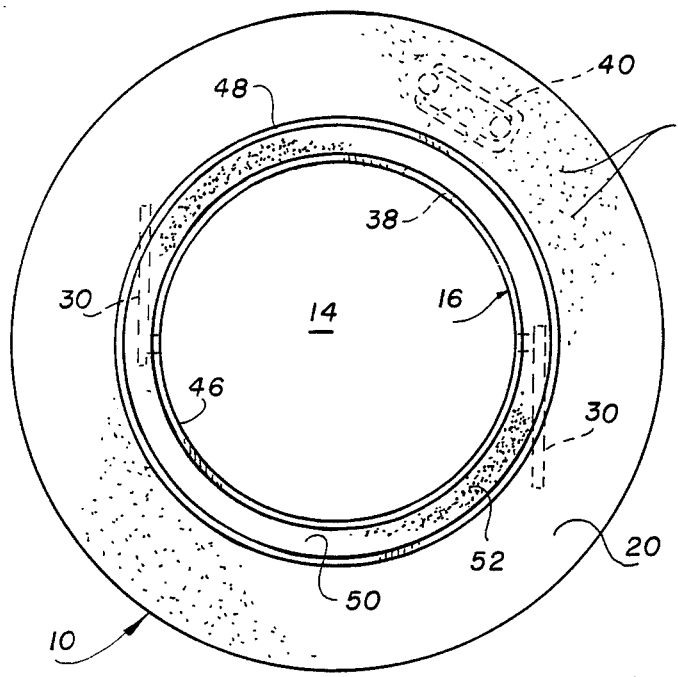
FIG. 4 is a bottom view of the support.
Figure 6:
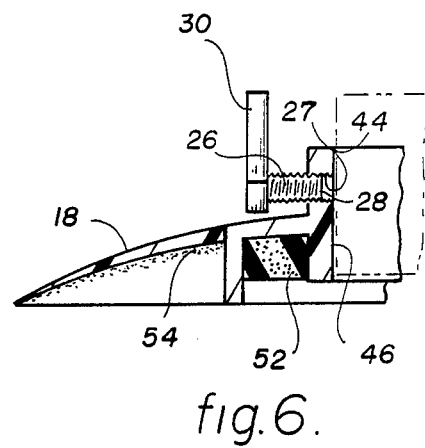
FIG. 6 is a sectional view of the grasping means taken along lines 6—6 of FIG. 5.

Referring to FIGS. 1 and 2, a substantially circular disc 10 of a relatively flexible material, such as rubber, is shown, having a central ultrasound transducer support member 12 made of a relatively rigid material, such as plastic. The support member 12 has a circular opening 14 therein. The disc 10 has a slightly concave shape so as to assist in conforming the disc 10 to the shape of the abdomen of the patient.

The support member has a wall 16 rising slightly above the top surface 18 and slightly below the lower surface 20 of the disc 10 for supporting an ultrasound transducer (not shown).

In the preferred embodiment of the present invention the circular opening 14 in the support member 12 is approximately 2½ inches in diameter, only slightly larger than the diameter of a standard ultrasound transducer used in the United States such as sold by Corometrics, Inc. The precise size of the opening will depend on the diameter of the ultrasound transducer desired to be used with the device.

The diameter of the disc 10 is approximately 5 inches. This has been found to be a highly acceptable size for use with most pregnant patients. The size of the disc 10 is sufficiently large to accommodate the distortions in the abdomen of the patient and still provide a stable base for the ultrasound transducer.

Figure 5:
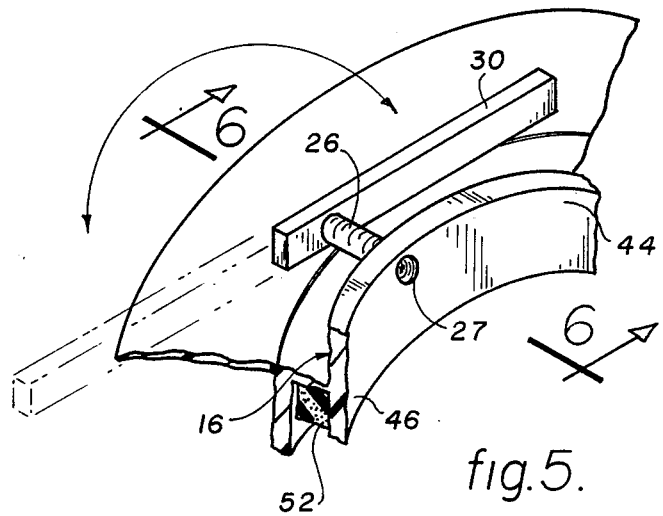
FIG. 5 is an expanded view of the grasping means of FIG. 1.

Two grasping members 22 and 24 are provided around the periphery of the opening. Details of the grasping members are shown in FIG. 4 and 5. The grasping members 22 and 24 provide means for grasping the ultrasound transducer to maintain the ultrasound transducer in position. The grasping means 22 and 24 are the same and consist of a threaded screws 26 having a blunted end 28 projecting through threaded openings 27 in the side wall 16 of the support member 12. The projecting screw 26 has a handle 30 for turning the screw 26. The screw 26 is normally in the retracted position so that the blunt end 28 of the screw 26 does not extend beyond the inside wall 16 of the support member 12. Upon rotation of the handle 30, the screw 26 is advanced so that it extends beyond the wall 10 of the support member 12. Upon turning the handle 30 in the other direction, the screw 26 is retracted. The handles 30 may be marked, either by use of a color indicator or other means, to indicate the extended or retracted position of the grasping members 22 and 24. While in the preferred version of the invention, two such grasping members 22 and 24 are employed, the number of such grasping members is a matter of choice and one such member may be used.

In addition to the grasping members 22 and 24 for grasping the ultrasound transducer itself, a cable grasping means 32 is provided for grasping the cable of the ultrasound transducer to limit movement and changes in the orientation of the ultrasound transducer. The cable grasping means 32 comprises two complementary support posts 34 and 36 extending perpendicularly from the top surface 18 of the disc 10. A gap 38 is provided in the wall 10 of the support member 12. A pivotal clasp 40 is attached to posts 34 which is capable of pivoting so as to engage an engaging means 42 on the other post 36.

In the preferred embodiment of the present invention, the posts 34 and 36 are about ½ inch high and spaced about ⅜ inches apart. The gap 38 is about ⅜ inch wide and ¼ inch deep. The size of the gap 38 and height of the posts 34 and 36 depend upon the size and position of the cable used on the ultrasound transducer.

The support member 12 has a portion 44 that extends above the top surface 18 and a portion 46 that extends below the lower surface 20 of the disc 10. In the preferred embodiment the support member is about ⅜ inches in height and extends about ¼ inches below the disc 10 and about ⅛ inches above the disc 10. The relatively rigid central support member 12 is attached at its periphery to the relatively flexible disc 10 by conventional molding operation.

The flexible disc 10 is made of soft plastic or rubber, while the relatively rigid central support member 12 is made of hard plastic, such as ABS.

Depending from the lower surface 20 of the disc 10 and spaced from the lower portion 44 of the support member 12 is a second relatively rigid annular member 48. In the preferred embodiment the second annular member 48 extends lower than the lower portion 46 of the support member 12. The annular portion 48 is approximately ¼ inch in length.

The space between the lower portion 46 and the annular member 48 forms a channel 50. An absorbent material 52, such as sponge or cotton, fills the channel 50 so as to provide a barrier to gel placed on the surface of the ultrasound transducer during use.

Medical grade adhesive 54 is applied to the lower surface 20 of the disc 10. The adhesive 54 must be strong enough to maintain the disc in a fixed position. Such medical grade adhesives are commonly used in medical practice. A protective removable paper covering (not shown) may cover the adhesive 54 until such time as it is desired to use the device. Alternatively, double-sided tape, shaped like a doughnut to conform to the shape of the flexible disc 10, may be used. Use of such tape could allow the device to be reusable.

In using the ultrasound transducer, a singular sequence of preparatory steps usually used with an ultrasound transducer are used. The location of the fetus is determined by conventional means. The adhesive protective layer is removed from the transducer holder and it is then applied to the location where it is desired to hold the ultrasound transducer. A small amount of ultrasonic coupling gel is then applied to the transducer face and the ultrasound transducer is then placed in the opening 14 in the holder and reoriented until the strongest signal is observed on the monitor. The cable of the ultrasound transducer is passed through the gap 38 and between posts 34 and 36 and the clasp 40 closed over the cable and locked in place by engaging means 42. The handles 30 of the grasping members 22 and 24 are then turned, advancing the screws 26 so that the blunt end 28 presses against the outer periphery of the ultrasound transducer, thereby holding the ultrasound transducer in a fixed orientation in relation to the patient.

The absorbent material 52 prevents the gel from coming into contact with the adhesive 54 maintaining the integrity of the position of the adhesive attachment. The channel 50, including the slightly longer second annular member 48, also serves to press against the abdomen of the patient preventing sliding of the transducer holder. A the same time, the skin of the patient on the abdomen is made to bulge up into the central opening 14, further restricting the ability of the holder to change position, acting as an isolation means.

While the holder is in place it has been found that it is possible for the patient to move, walk around and to even exercise enough so as to be subjected to an exercise stress test (a highly desirable test). The use of a belt system to hold the ultrasound transducer does not permit the acquisition of data in this situation.

In the preferred embodiment there is a slight spacing between the wall 16 of the holder and the ultrasound transducer. This permits any excess gel to pass up through the space, rather than be forced towards the bottom of the disc 10 where it might come into contact with the adhesive 54.

When it is desired to remove the ultrasound transducer, the handles 20 of the grasping means 22 and 24 are turned and the screws 26 are retracted. The clasp 40 is pivoted so as to release the cable and the ultrasound transducer can be removed. The holder is then removed from the patient. A solvent can be applied to the periphery of the disc 10 to weaken the adhesive so as to assist in the easy removal of the disc 10.

Figure 7:
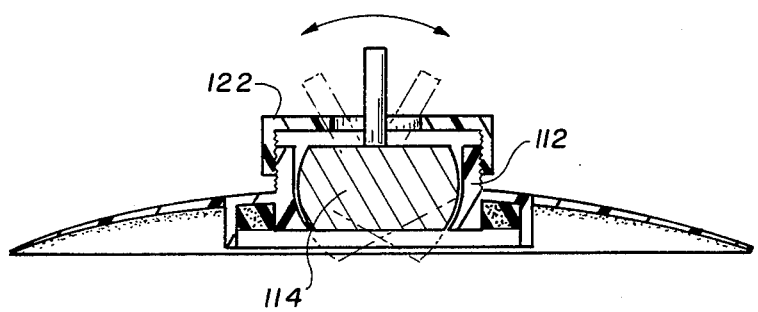
FIG. 7 is an alternate embodiment of the present invention.

While the preferred embodiment has been described in detail, it is recognized that other variations of the present invention may be devised without departing from the present concept. For example, a number of different grasping means may be devised for holding the cable, as well as for holding the ultrasound transducer in place. While a fixed ultrasound transducer support member has been found acceptable, the support member may be of a ball 114 and socket 112 arrangement as shown in FIG. 7. The ultrasound transducer is friction fitted into the opening 114 in the ball 110 and is rotated in three degrees of freedom to the desired orientation. Once in the proper orientation, the cap 122 is turned so as to compress the socket 112, fixing the ball 114 in place.

Other means for affixing an ultrasound transducer by adhesive to the patient are also possible. For example, surgical adhesive tape may be taped over the top surface 18 of the flexible disc 10 in order to hold the disc 10 in place. Such adhesive tape may be in strip form.

Also, the shape of the inside wall of the central support member may be curved so as to conform to the outside surface of the ultrasound transducer and still be able to be easily inserted into the opening.

Also, while the holder has been described as a disc, the term "disc" need not be limited to a circular member, but is meant to be a substantially flat object.

These and other variations of the present invention may be made which do not depart from the inventive concept.

What is claimed is:

1. A ultrasound transducer holder adapted for being adhesively applied to a patient comprising:
   (a) A relatively flexible concave disc having an upper surface and a lower surface and an opening therein;
   (b) A relatively rigid support member fixed to said flexible disc in the opening for supporting an ultrasound transducer in said opening; and
   (c) At least one grasping means for movably fixedly grasping said ultrasound transducer said grasping means capable of adjustably fixing the orientation of said ultrasound transducer relative to said support member.

2. The apparatus of claim 1, including adhesive means associated with the lower surface of said flexible disc for affixing said flexible disc to the body of a patient.

3. The apparatus of claim 1, in which said grasping means is movable between a first position and a second position, whereby when said grasping means is in said second position said transducer is fixed relative to said support member.

4. The apparatus of claim 1 in which the lower surface of said holder has a first relatively rigid depending member thereon surrounding said opening.

5. The apparatus of claim 4 in which said opening is centrally located and the lower surface of said flexible disc has a second relatively rigid depending member thereon, the space between said first and said second depending members defining a channel, and an absorbent material contained in said channel.

6. The apparatus of claim 5, including adhesive means associated with said disc for affixing said disc to a patient.

7. The apparatus of claim 6 in which said adhesive means is affixed to the lower surface of said disc.

8. The apparatus of claim 7 in which said support member has engaging means for engaging the cable of an ultrasound transducer.

9. The apparatus of claim 1 in which the diameter of said disc is approximately 5 inches.

10. The apparatus of claim 9 in which the opening in said support member is slightly larger than the outer diameter of the casing of an ultrasound transducer.

11. The apparatus of claim 10 in which said central opening is about 2½ inches.

12. The apparatus of claim 1 in which the diameter of said disc is about twice the diameter of the opening in said support member.

13. The apparatus of claim 1 in which said support member comprises a ball and socket, said ball including means for movably holding an ultrasound transducer.

14. The apparatus of claim 13 including means for removably fixing said ball to said socket.

15. The apparatus of claim 14 including adhesive means for affixing said disc to a patient.

16. A holder for an ultrasound transducer comprising a concave disc, said disc having an upper surface and a lower surface and a central opening therein for receiving an ultrasound transducer, said disc being adaptable to being adhesively applied to the body of a patient and holding means associated with said disc for removably and adjustably holding and maintaining an ultrasound transducer in a fixed relationship to the body of the patient.

17. The apparatus of claim 16 in which at least a portion of said disc is relatively flexible so as to conform to the shape of the body.

18. The apparatus of claim 17 in which said lower surface has a depending annular member extending therefrom.

19. The apparatus of claim 17 in which said lower surface has an absorbent material thereon surrounding said central opening.

20. The apparatus of claim 19 in which said absorbent material is maintained in a channel on said lower surface.

21. The apparatus of claim 16, including adhesive means applied to the lower surface of said disc.

22. The apparatus of claim 16 in which said means for holding an ultrasound transducer comprises a ball and socket, said ball having an opening therein for removably receiving the ultrasound transducer.

23. The apparatus of claim 16 including adhesive means applied to said disc for adhesively attaching said disc to the body of a patient.

24. An ultrasound transducer holder adapted for being adhesively applied to a patient comprising:
   (a) A relatively flexible disc capable of conforming to the shape of the patient having an upper surface and a lower surface and an opening therein;
   (b) A support member fixed to said flexible disc in the opening for supporting an ultrasound transducer in said opening; and
   (c) At least one grasping means for movably, fixedly grasping said ultrasound transducer, said grasping means capable of adjustably fixing the orientation of said ultrasound transducer relative to said support member.

25. The apparatus of claim 24 in which the lower surface of said holder has a first relatively rigid annular depending member thereon surrounding said opening.

26. The apparatus of claim 25 in which the lower surface of said flexible disc has a second relatively rigid annular depending member thereon, the space between said first and said second depending members defining a channel, and an absorbent material contained in said channel.

27. The apparatus of claim 24 in which said support member has a grasping means for grasping the cable of an ultrasound transducer.

28. The apparatus of claim 24 in which said support member comprises a ball and socket means, said ball including means for movably holding an ultrasound transducer.

* * * * *